United States Patent [19]

Cella

[11] Patent Number: 4,600,798
[45] Date of Patent: Jul. 15, 1986

[54] ARYL-DIETHERS

[75] Inventor: James A. Cella, Clifton Park, N.Y.

[73] Assignee: General Electric Company, Schenectady, N.Y.

[21] Appl. No.: 712,487

[22] Filed: Mar. 18, 1985

[51] Int. Cl.$^4$ .......................................... C07C 43/275
[52] U.S. Cl. ................... 568/636; 568/333; 568/33; 568/53; 564/433; 562/488; 549/241
[58] Field of Search ......................................... 568/636

[56] References Cited

FOREIGN PATENT DOCUMENTS 287791 10/1965 Australia ............................. 568/636

OTHER PUBLICATIONS

Koton et al., Chem. Abs., vol. 72 (1970), 90000p.
Lubowitz, Chem. Abs., vol. 75 (1971), 64581w.
W. M. Whaley, L. Starker, and M. Meadow, "A Synthetic Approach to Isotetradrine. I. 2,2',3-Trimethoxy-4',5-Dicarboxydiphenyl Ether", J. Org. Chem. 18 (1953), 833–834.

*Primary Examiner*—Bernard Helfin
*Attorney, Agent, or Firm*—Richard J. Traverso; James C. Davis, Jr.; James Magee, Jr.

[57] ABSTRACT

Aryl-diethers are provided which are produced by reacting a halogenated xylene compound, preferably 4-chloro-ortho-xylene, and an alkali metal salt of a bisphenol compound, preferably bisphenol-A. These aryl-diethers serve as precursors in a process for producing polyetherimide polymers.

4 Claims, No Drawings

ARYL-DIETHERS

This invention is directed to aryl-diethers derived from the salts of bisphenol compounds and methods for making polyetherimides therefrom. More particularly, this invention is directed to aryl-diethers of the formula:

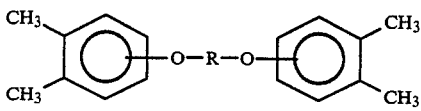

and methods for making polyetherimides by oxidation of these aryl-diethers and polymerizing the oxidized product with organic diamine. Polyetherimides are useful in forming films and wire coating enamels that are resistant to high temperatures. The divalent radical R, of formula I, is an organic radical of the general formula

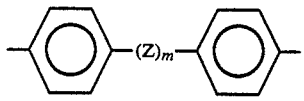

where Z is a member of the class consisting of divalent radicals of the formula $-C_yH_{2y}-$,

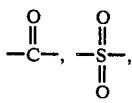

and $-S-$, $-O-$, and

m is 0 or 1, y is a whole number from 1 to 5 and R' is selected from alkyl radicals of from 1 to 5 carbon atoms.

A preferred class of aryl-diethers which are included by formula I are those wherein R is

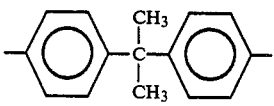

Included within this class of preferred aryl-diethers are those of the following formulas

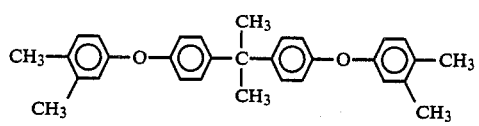

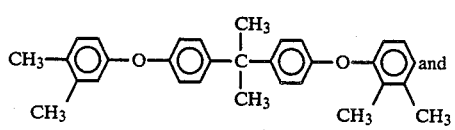

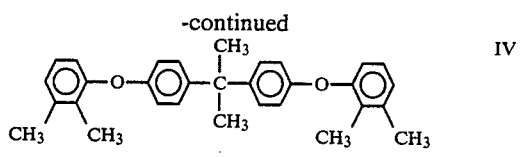

The aryl-diethers of formulas I–IV can be made by effecting reaction between the salt form of a bisphenol compound and halogenated xylenes. The salt form of the bisphenol compound is of the formula:

$$M^+ {}^-O-R-O^- {}^+M$$

wherein R is as previously defined and M is an alkali metal, preferably selected from the group consisting of sodium and potassium. The preferred halogenated xylenes are of the formulas

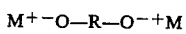

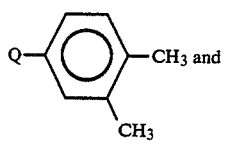

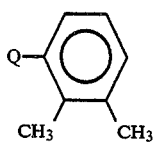

wherein Q is halogen, most preferably chlorine or bromine.

The halogenated xylenes and salts of bisphenol are reacted in the presence of a copper catalyst, such as a copper (I) salt at a temperature preferably above 100° C. Equimolar portions of the reagents are generally preferred but an excess of either reactant will also provide good yields of the aryl-diethers. A quantity of catalyst of about 1 to 30 mole percent based on halogenated xylenes provides acceptable yields, which often exceed 50%. Suitable copper salts are CuBr and CuCl.

The reaction typically takes place within a dipolar aprotic solvent, which is preferably an amide solvent such as dimethylacetamide, dimethylformamide or N—methyl-2-pyrrolidone. Mixtures of these solvents are suitable as are mixtures which contain other dipolar aprotic solvents. Reaction is most preferably accomplished within the range of about 150° to 200° C. for 2–4 hours.

The reaction products are recovered and purified by conventional techniques. These include ether extractions, distillation and column chromatography.

The halogenated xylenes are readily obtained by halogenation of xylenes as described by Wisansky and Ansbacher in *Organic Synthesis,* Coll. Vol. 3, page 198, incorporated herein by reference. The salts of bisphenol can be obtained by contacting an organic solution of the corresponding bisphenol compound with an aqueous solution of an alkali metal hydroxide, such as NaOH or KOH. An example of a suitable process is disclosed in U.S. Pat. No. 4,492,806; which is incorporated by reference. Typical bisphenol compounds include
2,2-bis-(2-hydroxyphenyl)propane;
2,4'-dihydroxydiphenylmethane;
bis-(2-hydroxyphenyl)-methane;

2,2-bis-(4-hydroxyphenyl)-propane hereinafter identified as "bisphenol-A" or "BPA";
1,1-bis-(4-hydroxyphenyl)-ethane;
1,1-bis-(4-hydroxyphenyl)-propane;
2,2-bis-(4-hydroxyphenyl)-pentane;
3,3-bis-(4-hydroxyphenyl)-pentane;
4,4'-dihydroxybiphenyl;
4,4'-dihydroxy-3,3',5,5'-tetramethylbiphenyl;
2,4-dihydroxybenzophenone;
4,4'-dihydroxydiphenyl sulfone;
2,4'-dihydroxydiphenyl sulfone;
4,4'-dihydroxydiphenyl sulfoxide;
4,4'-dihydroxydiphenyl sulfide; etc.

Included within the scope of this invention is a method for utilizing the aryl-diethers of formula I to prepare polyetherimides. The methyl radicals on the terminal aryl groups can be oxidized to form a tetra-acid or an aromatic bis(etheranhydride). An example of a tetra-acid obtained from the preferred aryl-diether of formula II is illustrated by formula V

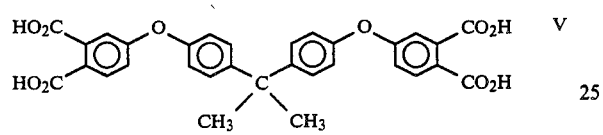

The aromatic bis(etheranhydride)s obtained from oxidizing aryl-diethers of formula I are illustrated by formula VI

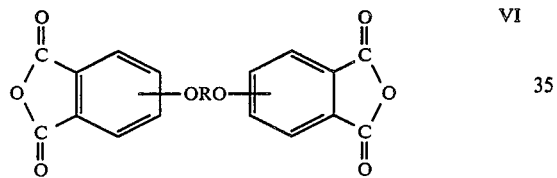

where R is as previously defined.

Oxidation of the terminal aryl groups can be achieved by aralkyl oxidation methods know to the art, which include reaction with oxygen in the presence of a metal-ion catalyst, such as manganese or cobalt. In U.S. Pat. No. 3,139,452, Hay discloses a process for reacting in liquid phase the alkyl group of an aralkyl compound with oxygen in the presence of a catalyst consisting essentially of a combination of cobalt, bromine and carboxylic acid at a temperature above 80° C. The contents of the Hay patent are incorporated herein by reference. A mixture of products may be obtained by this oxidation reaction, particularly where the divalent organic radical R has alkyl radicals bonded to its aromatic nuclei, as in the preferred species where R is derived from bisphenol-A. Oxidation may take place on these alkyl radicals as well.

The aryl-diethers in oxidized form can be polymerized to provide polyetherimides by reaction with an organic diamine of the formula $$H_2N-R^1-NH_2 \qquad VII$$

where $R^1$ is a divalent organic radical selected from the class consisting of
(a) aromatic hydrocarbon radicals having from 6-20 carbon atoms and halogenated derivatives thereof,
(b) alkylene radicals and cycloalkylene radicals having from 2-20 carbon atoms and (c) divalent radicals included within the scope of R as defined above by the formula

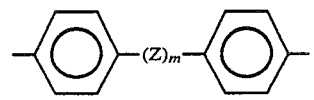

where Z and m are as previously defined.
Included within the organic diamines of formula VII are, for example,
m-phenylenediamine;
p-phenylenediamine;
4,4'-diaminodiphenylpropane;
4,4'-diaminodiphenylmethane;
benzidine;
4,4'-diaminodiphenyl sulfide;
4,4'-diaminodiphenyl sulfone;
4,4'-diaminodiphenyl ether;
1,5-diaminoaphthalene;
3,3'-dimethylbenzidine;
3,3'-dimethoxybenzidine;
2,4'-diaminotoluene; 2,6-diaminotoluene;
2,4-bis($\beta$-amino-t-butyl)toluene;
bis(p-$\beta$-methyl-o-aminopentyl)benzene;
1,3-diamino-4-isopropylbenzene;
1,2-bis(3-aminopropoxy)ethane;
m-xylylenediamine;
p-xylylenediamine;
bis(4-aminocyclohexyl)methane;
decamethylenediamine;
3-methylheptamethylenediamine;
4,4-dimethylheptamethylenediamine;
2,11-dodecanediamine;
2,2-dimethylpropylenediamene;
octamethylenediamine;
3-methoxyhexamethylenediamine;
2,5-dimethylhexamethylenediamine;
2,5-dimethylheptamethylenediamine;
3-methylheptamethylenediamine;
5-methylnonamethylenediamine;
1,4-cyclohexanediamine;
1,12-octadecanediamine;
bis(3-aminopropyl)sulfide;
N—methyl-bis(3-aminopropyl)amine;
hexamethylenediamine;
heptamethylenediamine; 2,4-diaminotoluene;
nonamethylenediamine; 2,6-diaminotoluene;
bis-(3-aminopropyl)tetramethyldisiloxane, etc. Polymerization of the oxidized aryl-diethers and diamines can be achieved with or without a solvent. Melt polymerization of the organic diamine can be accomplished at temperatures above about 200° C. and preferably less than 350° C. Takekoshi describes suitable melt polymerization processes with greater particularity in U.S. Pat. No. 3,833,546, which is incorporated herein by reference.

Solution polymerization is often more convenient than melt polymerization in that lower temperatures can be utilized. Dipolar aprotic solvents, such as dimethyl sulfoxide, N,N—dimethyl acetamide, N—methyl pyrrolidone, N,N—dimethyl formamide, N,N—diethyl formamide and the like, which are non-acid, nitrogen and/or oxygen containing solvents, are preferred. The term "dipolar aprotic solvent" is intended to mean any organic solvent which has no active protons which may interfere with the reaction herein described. Mixtures of dipolar aprotic solvents and other inert organic solvents, such as benzene, toluene, xylene and methylene chloride may also be used. Temperatures above about 100° C. are preferred for solution polymerization and are most preferably less than 300° C.

In order that those skilled in the art will be better able to practice the invention, the following examples are given by way of illustration and not by way of limitation. All parts are by weight.

EXAMPLE I

A solution of the dipotassium salt of bisphenol-A (0.76 g, 2.5 mmol); 4-bromo-ortho-xylene (1.11 mg, 6.0 mmol) and the copper chloride salt, CuCl, (37.1 mg, 0.38 mmol) in N—methyl-2-pyrrolidone was heated with stirring in a flask immersed in an oil bath at about 175° C. for 3 hours. The cooled mixture was diluted with ether (about 60 ml) and water (about 30 ml) and transferred to a separatory funnel. The diluted solution was washed with HCl (30 ml, 1.0 N) followed by NaOH (30 ml, 1 N) and then a brine wash. The ethereal solution was dried by passage through a cone of anhydrous CaSO$_4$ and the ether was removed by distillation at reduced pressure. The residue (1.09 g) was chromatographed on 75 g of silicon gel diluted with 5% ethyl acetate/hexane to afford 776 mg (71.2% yield) of an aryl-diether of formula I. Proton NMR in CDCl$_3$ gave peaks at 6.90 (multiplet), 2.05 (singlet) and 1.51 (singlet) ppm. The intensities were 14.12 and 6, respectively. The peaks at 2.05 ppm and 1.51 ppm are consistent with methyl-aromatic nuclei and methy-gem nuclei, respectively.

EXAMPLE II

A solution of the disodium salt of bisphenol-A (75 mmol), 4-bromo ortho xylene (80 mmol) and a copper chloride salt, CuCl, (2.5 mole %) in N—methyl-2-pyrrolidone (ca. 100 ml) was heated with stirring in an oil bath at about 150° C. for about 2–4 hours. The cooled mixture was diluted with ether (about 60 ml) and transferred to a separating funnel where the organic phase was washed with water (30 ml), HCl (1.0 N, 30 ml) and brine. The ether extracts were dried by passage through a cone of anhydrous CaSO$_4$. The ether was removed by distillation at reduced pressure and the residue purified by column chromatography. The isolated yield of the aryl-diether of formula I was 48.6%.

What is claimed is:

1. An aryl-diether of the formula

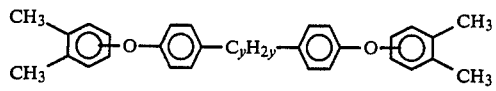

wherein y is a whole number from 1 to 5.

2. An aryl-diether of a formula selected from the group consisting of

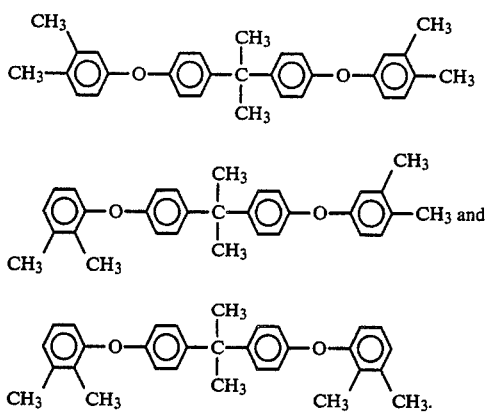

3. An aryl-diether of claim 2 obtained by reacting a halogenated xylene of a formula selected from the group consisting of

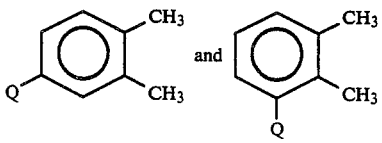

and an alkali metal salt of bisphenol-A having the formula

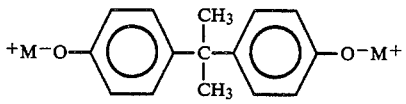

where Q is halogen and M is an alkali metal in the presence of a copper catalyst.

4. An aryl-diether of claim 3 wherein Q is selected from the group consisting of chlorine and bromine and M is selected from the group consisting of sodium and potassium.

* * * * *